US011331054B2

United States Patent
Adachi et al.

(10) Patent No.: US 11,331,054 B2
(45) Date of Patent: May 17, 2022

(54) BIOLOGICAL INFORMATION MEASURING INSTRUMENT, AND METHOD, DEVICE, AND COMPUTER-READABLE STORAGE MEDIUM CONTAINING A PROGRAM FOR CONTROLLING THE INSTRUMENT

(71) Applicant: Sharp Kabushiki Kaisha, Osaka (JP)

(72) Inventors: Yoshihisa Adachi, Sakai (JP); Tetsuya Okumura, Sakai (JP); Takashi Nunokawa, Sakai (JP); Rieko Ogawa, Sakai (JP); Yuki Edo, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 543 days.

(21) Appl. No.: 16/344,844

(22) PCT Filed: Oct. 31, 2017

(86) PCT No.: PCT/JP2017/039442
§ 371 (c)(1),
(2) Date: Apr. 25, 2019

(87) PCT Pub. No.: WO2018/084157
PCT Pub. Date: May 11, 2018

(65) Prior Publication Data
US 2020/0046301 A1    Feb. 13, 2020

(30) Foreign Application Priority Data
Nov. 7, 2016   (JP) .............................. JP2016-217488

(51) Int. Cl.
*A61B 5/00*    (2006.01)
*G06F 3/01*    (2006.01)

(52) U.S. Cl.
CPC ............ *A61B 5/7405* (2013.01); *A61B 5/746* (2013.01); *G06F 3/015* (2013.01); *G06F 3/017* (2013.01); *G06F 2203/011* (2013.01)

(58) Field of Classification Search
CPC ........ A61B 5/7405; G06F 3/015; G06F 3/017
(Continued)

(56) References Cited

U.S. PATENT DOCUMENTS 7,881,780 B2 *   2/2011   Flaherty .................. G06F 3/015
                                                           600/544
9,262,612 B2 *   2/2016   Cheyer .................... G06F 21/32
(Continued)

FOREIGN PATENT DOCUMENTS

CN    102764110 A    11/2012
CN    204971255 U     1/2016
(Continued)

OTHER PUBLICATIONS

Official Communication issued in International Patent Application No. PCT/JP2017/039442, dated Dec. 19, 2017.

*Primary Examiner* — Calvin C Ma
(74) *Attorney, Agent, or Firm* — Keating & Bennett, LLP

(57) ABSTRACT

A biological information measuring instrument performs high precision biological information measurement on a living body. The biological information measuring instrument includes: a measuring unit and an analysis unit that measure a user in a contactless manner to acquire biological information; and a speech unit that produces an alarm for reducing body movements of the user. The measuring unit and the analysis unit start to acquire biological information at an acquisition starting time. A control unit sets the acquisition starting time so as to fall in a prescribed range of time defined using an alarm starting time for the speech unit as a reference.

16 Claims, 11 Drawing Sheets

(58) Field of Classification Search
USPC .................................. 600/300; 345/173–174
See application file for complete search history.

(56) References Cited

U.S. PATENT DOCUMENTS

| | | | | |
|---|---|---|---|---|
| 2014/0004828 A1* | 1/2014 | Han | ............... | H04W 64/00 |
| | | | | 455/411 |
| 2018/0042486 A1 | 2/2018 | Yoshizawa et al. | | |
| 2018/0232056 A1* | 8/2018 | Nigam | ............... | G06F 3/013 |

FOREIGN PATENT DOCUMENTS

| | | |
|---|---|---|
| JP | 5-200004 A | 8/1993 |
| JP | 7-116135 A | 5/1995 |
| JP | 2005-034484 A | 2/2005 |
| JP | 2006-285425 A | 10/2006 |
| JP | 2010-240458 A | 10/2010 |
| JP | 2013-34499 A | 2/2013 |
| WO | 2016/158624 A1 | 10/2016 |

* cited by examiner

BIOLOGICAL INFORMATION MEASURING INSTRUMENT, AND METHOD, DEVICE, AND COMPUTER-READABLE STORAGE MEDIUM CONTAINING A PROGRAM FOR CONTROLLING THE INSTRUMENT

TECHNICAL FIELD

The following disclosure relates to, for example, biological information measuring instruments for taking measurements of a living body for biological information.

BACKGROUND ART

Various techniques have been proposed for taking measurements of a living body (e.g., human or user) to acquire biological information on the living body. Patent Literature 1, as an example, discloses a health care service system one of objects of which is to enable the user to more reliably take measurements for biological information (e.g., blood pressure) using a biosensor (e.g., blood pressure meter).

More specifically, Patent Literature 1 discloses a health care service system involving the use of a robot capable of producing a database of the user's pattern of living. As the time arrives when the user is expected to wear or attach a biosensor to take measurements for biological information, the robot carries out conversation to prompt the user to take such measurements. The health care service system of Patent Literature 1 controls the robot in this manner, so that the robot can prevent the user from forgetting to attach a biosensor.

CITATION LIST

Patent Literature

Patent Literature 1: Japanese Unexamined Patent Application Publication, Tokukai, No. 2006-285425A (Publication Date: Oct. 19, 2006)

SUMMARY OF THE INVENTION

Problems to be Solved by the Invention

To take measurements for biological information that faithfully reflects the condition of the living body, the measurements are preferably taken without making the living body consciously aware of the measurement. In other words, the measurements are preferably taken while the living body is in a condition that is close to a natural condition thereof (hereinafter, may be referred to as a "semi-natural condition").

The health care service system of Patent Literature 1 however requires a measuring instrument (biosensor) to be attached to the living body by himself/herself before taking measurements of the living body. The living body is therefore highly aware of the measurement when the measurement of the living body is to be started. It is hence difficult to acquire biological information on the living body in a semi-natural condition if the measuring instrument used needs to be brought into contact with the living body to take measurements of the living body (i.e., if the measurements are taken using a "contact-type measuring instrument").

On the other hand, if the living body is measured in a contactless manner (using a non-contact measuring instrument), the measuring instrument does not need to be attached to the living body, which enables the measurement without making the living body consciously aware of the measurement being performed. Contactless measurement is therefore preferred in taking measurements of the living body in order to acquire biological information on the living body in a semi-natural condition.

Meanwhile, in contactless measurement of the living body, the living body is not consciously aware of the measurement and tends to make relatively large body movements. These large body movements of the living body during measurement could lead to large measurement errors. High precision measurement of the living body for biological information is therefore difficult to perform if the measurement is performed in a contactless manner (i.e., if the living body is in a semi-natural condition).

Contact measurement of the living body is still possible without making the living body consciously aware of the measurement, depending on how the measurement is performed, as described later. The living body may make relatively large body movements in contact measurement as in contactless measurement. These large body movements of the living body during measurement could also lead to large measurement errors in the acquired biological information.

The present disclosure, in an aspect thereof, has been made in view of these issues and has an object to achieve high precision measurement of a living body to acquire biological information on the living body.

Solution to Problem

To address the issues, the present disclosure, in one aspect thereof, is directed to a biological information measuring instrument including: a biological information acquisition unit configured to measure a living body to acquire biological information on the living body; an alarm unit configured to produce an alarm calling for attention from the living body; and a control unit configured to control the biological information acquisition unit and the alarm unit, wherein: the alarm unit starts the alarm at an alarm starting time and ends the alarm at an alarm ending time; the biological information acquisition unit starts acquisition of the biological information at an acquisition starting time; and the control unit sets the acquisition starting time so as to fall in a prescribed range of time defined using the alarm starting time as a reference.

To address the issues, the present disclosure, in another aspect thereof, is directed to a method of controlling a biological information measuring instrument including: a biological information acquisition unit configured to measure a living body to acquire biological information on the living body; and an alarm unit configured to produce an alarm calling for attention from the living body, the method including the control step of controlling the biological information acquisition unit and the alarm unit, wherein: the alarm unit starts the alarm at an alarm starting time and ends the alarm at an alarm ending time; the biological information acquisition unit starts acquisition of the biological information at an acquisition starting time; and the control step includes setting the acquisition starting time so as to fall in a prescribed range of time defined using the alarm starting time as a reference.

To address the issues, the present disclosure, in a further aspect thereof, is directed to a control device that controls a biological information measuring instrument including: a biological information acquisition unit configured to measure a living body to acquire biological information on the living body; and an alarm unit configured to produce an alarm calling for attention from the living body, the control device including a control unit configured to control the biological information acquisition unit and the alarm unit, wherein: the alarm unit starts the alarm at an alarm starting time and ends the alarm at an alarm ending time; the biological information acquisition unit starts acquisition of the biological information at an acquisition starting time; and the control unit sets the acquisition starting time so as to fall in a prescribed range of time defined using the alarm starting time as a reference.

Advantageous Effects of Invention

A biological information measuring instrument of an aspect of the present disclosure performs high precision biological information measurement on a living body.

A method of controlling a biological information measuring instrument of an aspect of the present disclosure and a control device of an aspect of the present disclosure achieves a similar advantage.

DESCRIPTION OF EMBODIMENTS

Embodiment 1

Figure 1:
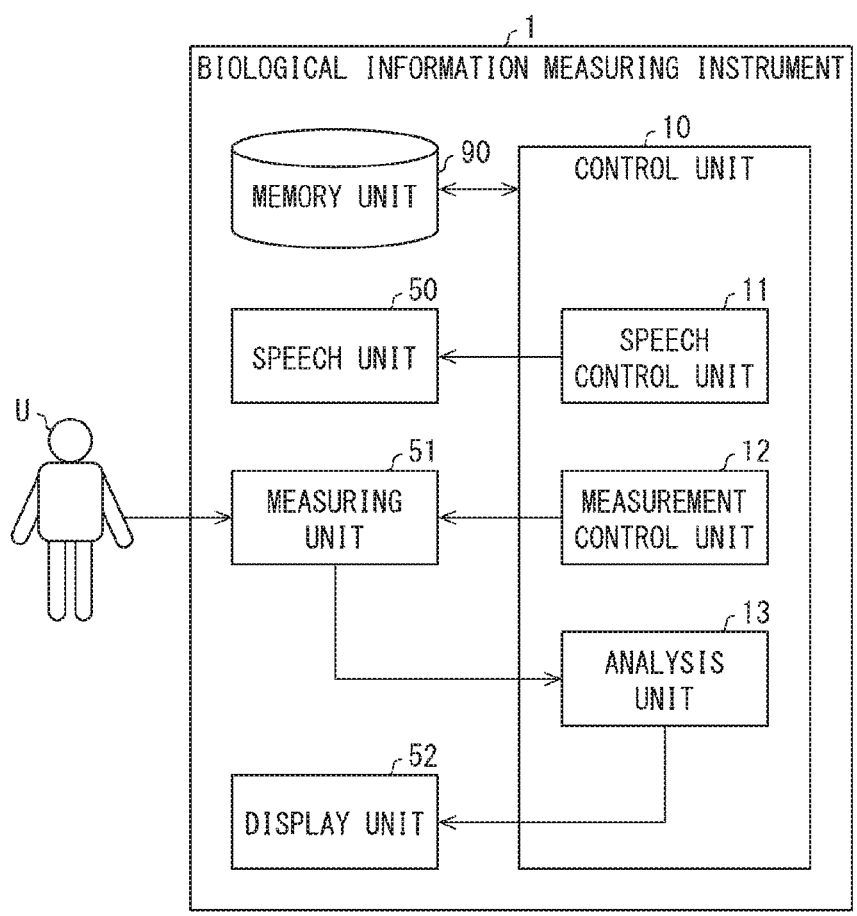
FIG. 1 is a functional block diagram of a configuration of major components of a biological information measuring instrument in accordance with Embodiment 1.

The following will describe Embodiment 1 in detail in reference to FIGS. 1 to 4. A general description will be given first of a biological information measuring instrument 1 in accordance with Embodiment 1 in reference to FIG. 1. FIG. 1 is a functional block diagram of a configuration of major components of the biological information measuring instrument 1.

Biological Information Measuring Instrument 1

The biological information measuring instrument 1 is a device for taking measurements of a living body to acquire biological information on the living body. Embodiment 1 primarily illustrates, as an example, the biological information measuring instrument 1 performing contactless biological information measurement. Alternatively, the biological information measuring instrument 1 may perform contact measurement for biological information as will be mentioned later in the description.

The biological information measuring instrument 1 may be installed, for example, in a robot capable of voice conversation (communication robot). The biological information measuring instrument 1 may however be installed in any other type of apparatus, including home electrical appliances, in-vehicle devices, information processing devices, and mobile terminals. The apparatus needs only to allow a user U ("living body" or human) to face the apparatus for a period of time (measurement period).

Embodiment 1 illustrates, as an example, the biological information measuring instrument 1 performing biological information measurement on the user U. The living body on which the biological information measuring instrument 1 performs measurement is not necessarily a human. The measurement may be performed on any living body from which a biological information acquisition unit (detailed later) can acquire biological information. The living body may be, for example, a dog, a cat, or any other animal.

Biological information is information (indicator) representing the physiological condition of a living body and may be, for example, information used in health management of the user U. Specific examples of biological information in Embodiment 1 include a pulse wave (plethysmogram), heart rate, blood pressure, respiration rate, and stress level of the user U. A plethysmogram is a waveform representing the pulsation of blood vessels that accompanies the ejection of blood from the heart.

Referring to FIG. 1, the biological information measuring instrument 1 includes a control unit 10 (control device), a speech unit 50 (alarm unit, aural alarm unit), a measuring unit 51 (biological information acquisition unit), a display unit 52, and a memory unit 90. The control unit 10 generally controls each component of the biological information measuring instrument 1. The functions of the control unit 10 may be implemented by a CPU (central processing unit) executing programs contained in the memory unit 90. Specific operations of the control unit 10 will be described later. The memory unit 90 contains various programs executed by the control unit 10 and data used in the programs.

The speech unit 50 produces an audio speech and may be, for example, a speaker. More specifically, the speech unit 50 reproduces voice and/or sound from prescribed speech data for output. The speech data may be either stored in advance in the memory unit 90 or generated automatically in a speech control unit 11 (detailed later) by a known technique. The provision of the speech unit 50 imparts to the biological information measuring instrument 1 a speech function aimed at the user U.

The speech unit 50 plays the role of an alarm unit (aural alarm unit) that aurally calls for attention from the user U through its speech in biological information measurement as detailed in the following. The alarm unit is a functional unit that performs a prescribed operation (alarm operation, alarming) to call for attention from the user U. Embodiment 1 illustrates, as an example, the speech unit 50 performing a speech as an alarm operation.

To take measurements of the user U in a semi-natural condition for biological information, the content of the speech data (the content of the speech performed by the speech unit 50) preferably makes the user U as little aware of the biological information measurement being performed as possible (the content should to the least possible extent be suggestive of the biological information measurement). Therefore, the content of the speech data is preferably, for example, a greeting, news, or schedule information.

However, if the content of the speech data is something that makes the user U aware of the biological information measurement (something suggestive of the measurement), the acquisition of biological information on the user U in a semi-natural condition is still possible. An example will be described later in detail (see (b) of FIG. 2).

The measuring unit 51 takes measurements of the user U. Embodiment 1 primarily illustrates, as an example, the measuring unit 51 performing contactless measurement on the user U. The provision of the measuring unit 51 that performs contactless measurement on the user U enables suitable biological information measurement of the user U in a semi-natural condition as described earlier. The measuring unit 51 however may perform contact measurement on the user as described later.

Embodiment 1 illustrates, as an example, the measuring unit 51 being an imaging device (camera) that captures images of a prescribed body part (e.g., face) of the user U without restraining the movement of the user U. Accordingly, the measuring unit 51 obtains a moving image by capturing images of the face of the user U. The measuring unit 51 then supplies the moving image as a result of measurement to the control unit 10 (more specifically, to an analysis unit 13 (biological information acquisition unit) which will be described later). The measurement performed by the measuring unit 51 may alternatively be referred to as the "biological information measurement" for convenience of description throughout Embodiment 1.

The display unit 52 is, for example, a liquid crystal display device. The display unit 52 graphically displays various information. As an example, the display unit 52 may graphically display the biological information supplied from the control unit 10 (more specifically, the result of analysis supplied from the analysis unit 13). In other words, the display unit 52 may function as a notification unit that visually notifies the user U of the biological information.
Control Unit 10

A more specific description is now given of the control unit 10. The control unit 10 includes the speech control unit 11, a measurement control unit 12, and the analysis unit 13. The speech control unit 11 controls the operation of the speech unit 50. The measurement control unit 12 controls the operation of the measuring unit 51.

More specifically, (i) the speech control unit 11 sets start and end timings for a speech performed by the speech unit 50, and (ii) the measurement control unit 12 sets start and end timings for measurement performed by the measuring unit 51. Specific examples of the timings will be described later.

The analysis unit 13 analyzes the result of measurement (moving image) acquired from the measuring unit 51 to acquire biological information. The analysis unit 13 may supply the acquired biological information to the display unit 52. Alternatively, the analysis unit 13 may supply the biological information to a device outside the biological information measuring instrument 1 (e.g., to a cloud server connected communicably to the biological information measuring instrument 1).

The measuring unit 51 and the analysis unit 13 may be collectively called a biological information acquisition unit (i.e., a functional unit that takes measurements of the user U and acquires biological information on the user U). Embodiment 1 illustrates, as an example, the measuring unit 51 and the analysis unit 13 being provided as separate functional units. Alternatively, the measuring unit 51 may double as the analysis unit 13. That is, the biological information acquisition unit may be provided as an integrated single functional unit.

The analysis unit 13 in Embodiment 1 analyzes the moving image acquired from the measuring unit 51 to acquire a pulse wave (first biological information). Additionally, the analysis unit 13 may further analyze the pulse wave as described in the following, to acquire biological information (second biological information) that differs from a pulse wave. A description is given next of example operations of the analysis unit 13.

First, the analysis unit 13 decomposes the moving image into frames to generate frame images. The analysis unit 13 then specifies face regions (regions for the face of the user U) in the frame images, one face region for every predetermined number of frames. The analysis unit 13 may specify face regions by a known face detection algorithm.

Subsequently, the analysis unit 13 calculates a pulse wave in the face regions by a known technique. For example, the analysis unit 13 detects a luminance for each color (e.g., RGB (red, green, and blue)) and for each pixel in the face regions for every predetermined number of frames. In other words, the analysis unit 13 detects a signal representing temporal changes of luminance over a prescribed period. The analysis unit 13 then performs a known mathematical process on the signal to calculate a pulse wave.

The analysis unit 13, as described above, may further analyze the pulse wave by a known technique to acquire second biological information. The second biological information may be, for example, any one of heart rate, blood pressure, and stress level. In this example, the pulse wave (first biological information) may be regarded as information (biological information) related to at least one of heart rate, blood pressure, and stress level.

(1) For example, the analysis unit 13 may count the number of peaks on the pulse wave to calculate the number of peaks as a heart rate.

(2) The analysis unit 13 may alternatively differentiate the pulse wave twice with respect to time to calculate an acceleration plethysmogram (second derivative of photoplethysmogram). In these cases, the analysis unit 13 can acquire a conventional feature quantity (e.g., amplitude) from the acceleration plethysmogram and calculate blood pressure from the feature quantity.

(3) As a further alternative, the analysis unit 13 may acquire a pulse wave of the user U from at least two sites on his/her body. The analysis unit 13 may calculate a temporal difference of the pulse wave between the two sites (pulse wave propagation time). In these cases, the analysis unit 13 can calculate blood pressure on the basis of known data (e.g., calculation formula) that represents a relationship between pulse wave propagation time and blood pressure.

If the distance between the sites is known, the analysis unit 13 may calculate the velocity (pulse wave propagation velocity) at which the pulse wave is transmitted between the sites. In these cases, the analysis unit 13 can calculate blood pressure on the basis of known data (e.g., calculation formula) that represents a relationship between pulse wave propagation velocity and blood pressure.

(4) As a further alternative, the analysis unit 13 may subject a time interval between one pulse wave and the next to FFT (fast Fourier transform) to calculate a power spectrum. The analysis unit 13 can then analyze the power spectrum by a known technique to calculate a stress level. It is known that the low frequency components (attributable to changes in blood pressure that have approximately 10-second cycles) and high frequency components (attributable to respiration with approximately 3- to 4-second cycles) of the power spectrum are generally closely related with the stress level.

"Stress" in Embodiment 1 refers to a balance of activity between the sympathetic nervous system and the parasympathetic nervous system. Specifically, if the sympathetic nervous system is more active than the parasympathetic nervous system, that condition is referred to as the "stressful state." On the other hand, if the parasympathetic nervous system is more active than the sympathetic nervous system, the condition is referred to as the "relaxed state."

As an example, the analysis unit 13 calculates the value, LF, of an integral of the power spectrum over low frequencies from 0.04 Hz to 0.15 Hz. LF is an indicator of the activity level of the sympathetic nervous system. The analysis unit 13 also calculates the value, HF, of an integral of the power spectrum over high frequencies from 0.15 to 0.4 Hz. HF is an indicator of the activity level of the parasympathetic nervous system.

The analysis unit 13 may calculate a value LF/HF as a stress level. A small LF/HF value (low stress level) indicates that the user U is in a relaxed state. On the other hand, a large LF/HF value (high stress level) indicates that the user U is in a stressful state.

Example Timings of Speech and Biological Information Measurement

Figure 2:
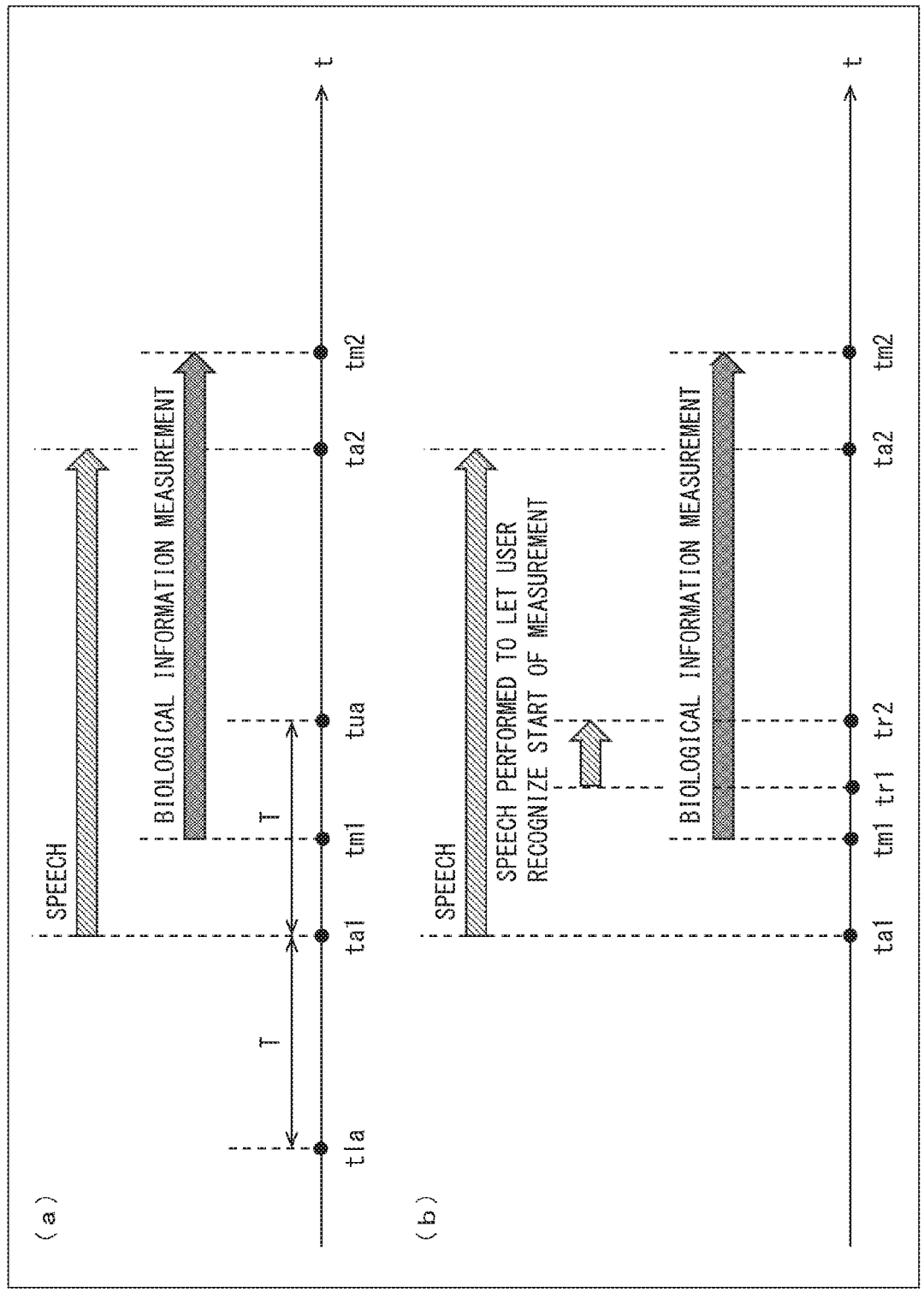
FIG. 2, in each portion (a) and (b) thereof, shows example timings of a speech and biological information measurement in the biological information measuring instrument shown in FIG. 1.

Portions (a) and (b) of FIG. 2 are timing charts showing example timings of a speech performed by the speech unit 50 and biological information measurement performed by the measuring unit 51 in the biological information measuring instrument 1. The example shown in (a) of FIG. 2 is described first. The example shown in (b) of FIG. 2 will be described later. Time (point in time) is denoted by a symbol "t" in FIG. 2.

Referring to (a) of FIG. 2, the speech control unit 11 sets (i) a starting time for a speech performed by the speech unit 50 to time ta1 and (ii) an ending time for that speech by the speech unit 50 to time ta2. In the rest of the description, time ta1 may be referred to as a speech starting time (alarm starting time, aural alarm starting time), and time ta2 may be referred to as a speech ending time (alarm ending time, aural alarm ending time).

The measurement control unit 12 also sets (i) a starting time for measurement performed by the measuring unit 51 (biological information measurement) to time tm1 and (ii) an ending time for that measurement by the measuring unit 51 to time tm2. In the rest of the description, time tm1 may be referred to as a measurement starting time (acquisition starting time), and time tm2 may be referred to as a measurement ending time (acquisition ending time). Measurement starting time tm1 may be regarded as a time when the biological information acquisition unit starts acquiring biological information on the user U. Likewise, measurement ending time tm2 may be regarded as a time when the biological information acquisition unit ends acquiring biological information on the user U.

The measurement control unit 12 further sets measurement starting time tm1 so as to fall in a prescribed range of time defined using speech starting time ta1 as a reference and sets measurement starting time tm1 so as to come before speech ending time ta2.

Specifically, referring to (a) of FIG. 2, the measurement control unit 12 sets measurement starting time tm1 so as to satisfy mathematical expressions (1) and (2).

$$tla \leq tm1 \leq tua \quad (1)$$

$$tm1 < ta2 \quad (2)$$

Note that $tla = ta1 - \alpha 1$ in mathematical expression (1), where tla may be referred to as the earliest speech starting reference time. Note also that $tua = ta1 + \alpha 2$ in mathematical expression (1), where tua may be referred to as the last speech starting reference time.

Measurement starting time tm1 needs only to be set so as to satisfy mathematical expression (1) above in the biological information measuring instrument in an aspect of the present disclosure. In other words, satisfying mathematical expression (2) is not an essential condition in the biological information measuring instrument in an aspect of the present disclosure. It is however preferable, in view of improved precision of the measurement, that measurement starting time tm1 be set so as to satisfy mathematical expression (2) as well as mathematical expression (1) as detailed later. Embodiment 1 illustrates, as an example, measurement starting time tm1 being set so as to satisfy both mathematical expressions (1) and (2).

The values of $\alpha 1$ and $\alpha 2$ in mathematical expression (1) may be predetermined in the biological information measuring instrument 1. The measurement control unit 12 sets tla and tua using the predetermined values of $\alpha 1$ and $\alpha 2$ in reference to speech starting time ta1. The value of $\alpha 2$ needs to be set by taking mathematical expression (2) above into consideration so as to satisfy tua<ta2.

Embodiment 1 illustrates an example where $\alpha 1 = \alpha 2 = T$ for the purpose of simplicity. In other words, the measurement control unit 12 sets measurement starting time tm1 so as to fall in a temporal range ta1±T in Embodiment 1.

Measurement starting time tm1 is set so as to satisfy ta1<tm1, and measurement ending time tm2 is set so as to satisfy ta2<tm2, in the example shown in (a) of FIG. 2. In other words, in the biological information measuring instrument 1, (i) the speech unit 50 starts a speech before the measuring unit 51 starts measurement, and (ii) the speech unit 50 ends the speech before the measuring unit 51 ends the measurement, as an example.

Flow of Process of Biological Information Measurement in Biological Information Measuring Instrument 1

Figure 3:
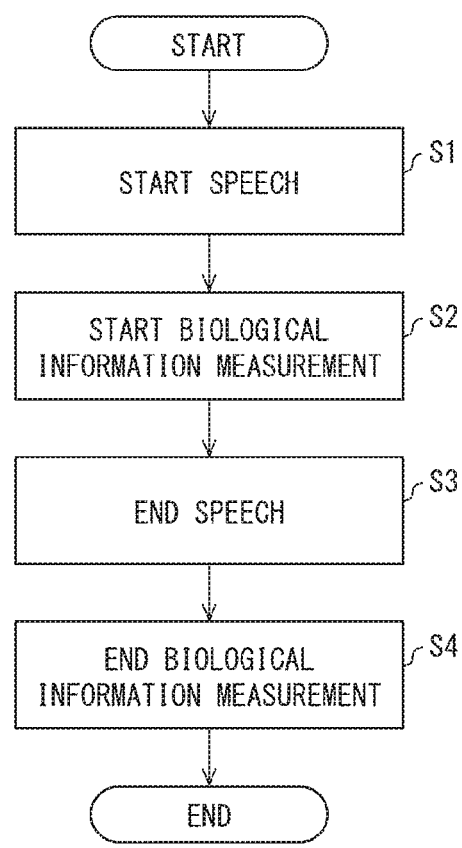
FIG. 3 is a diagram showing an example flow for a process of biological information measurement in the biological information measuring instrument shown in FIG. 1.

FIG. 3 is a flow chart of an example flow of a process S1 to S4 (control steps) of biological information measurement in the biological information measuring instrument 1. FIG. 3 shows, as an example, a flow of a process where measurement starting time tm1 and measurement ending time tm2 are set so as to satisfy ta1<tm1 and ta2<tm2 as shown in (a) of FIG. 2.

First, the speech control unit 11 controls the speech unit 50 to start a speech at speech starting time ta1 (S1). Subsequently, the measurement control unit 12 controls the measuring unit 51 to start measurement at measurement starting time tm1 (S2).

Thereafter, the speech control unit 11 controls the speech unit 50 to end the speech at speech ending time ta2 (S3).

Subsequently, the measurement control unit 12 controls the measuring unit 51 to end the measurement at measurement ending time tm2 (S4).

Other Example Timings of Speech and Biological Information Measurement

Figure 4:
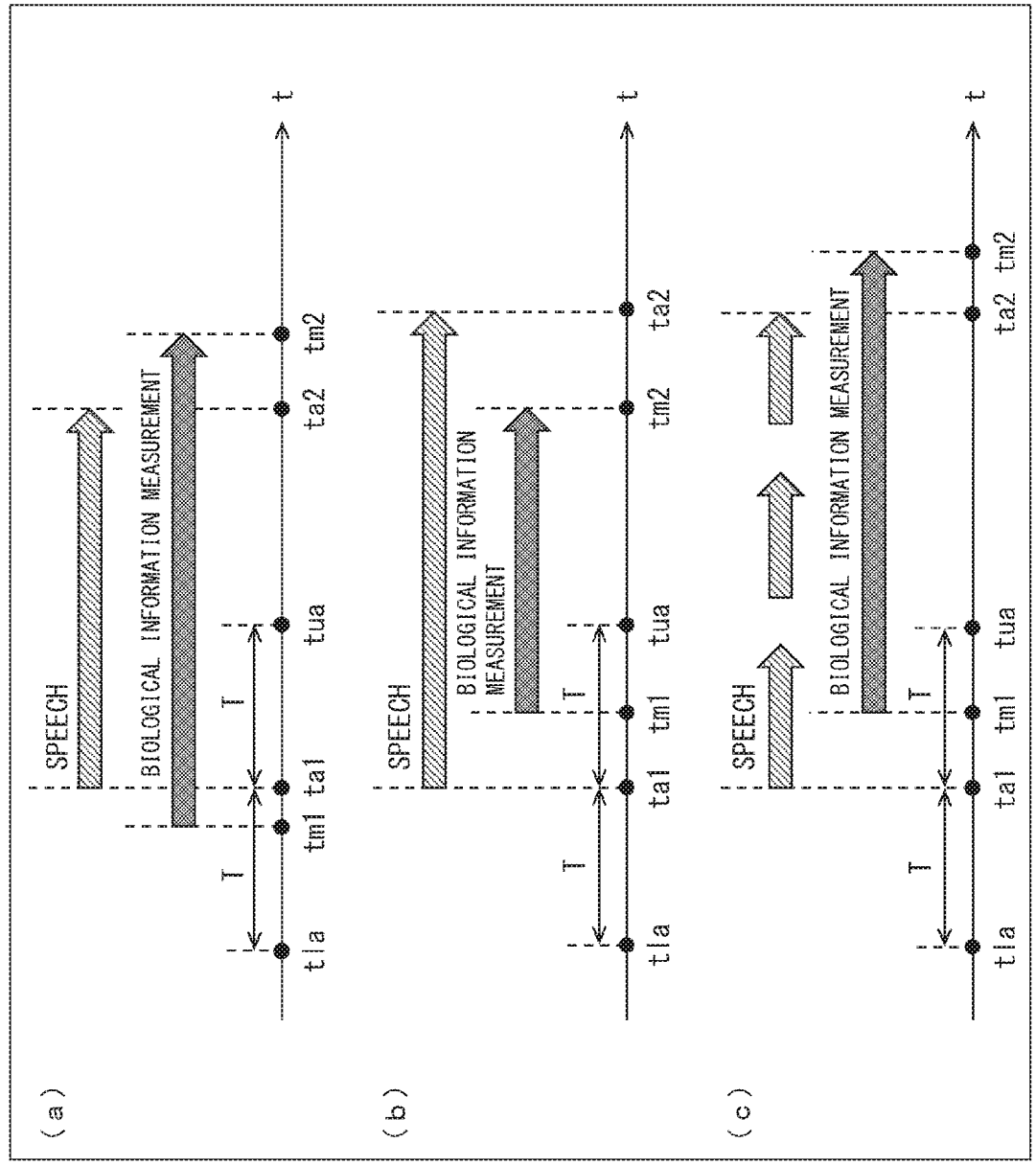
FIG. 4, in each portion (a) to (c) thereof, shows other example timings of a speech and biological information measurement in the biological information measuring instrument shown in FIG. 1.

The speech unit 50 and the measuring unit 51 do not necessarily perform a speech and biological information measurement respectively at the timings given in the example shown in (a) of FIG. 2. Portions (a) to (c) of FIG. 4 are timing charts showing other example timings.

(1) Measurement starting time tm1 is set so as to satisfy ta1<tm1 in (a) of FIG. 2. Measurement starting time tm1, however, needs only to be set so as to satisfy mathematical expressions (1) and (2). Therefore, measurement starting time tm1 may be set so as to satisfy tm1<ta1 as shown in (a) of FIG. 4. In other words, the measuring unit 51 may start measurement before the speech unit 50 starts a speech.

(2) Measurement ending time tm2 is set so as to satisfy ta2<tm2 in (a) of FIG. 2. Measurement ending time tm2 may be set so as to satisfy tm2<ta2 as shown in (b) of FIG. 4. In other words, the measuring unit 51 may end measurement before the speech unit 50 ends a speech.

(3) The speech control unit 11 controls the speech unit 50, as an example, to perform a speech continuously over a time period (speech time period) ta1≤t≤ta2 in (a) of FIG. 2. Alternatively, the speech control unit 11 may control the speech unit 50 to perform a speech intermittently in the speech time period as shown in (c) of FIG. 4.

In other words, the speech time period may contain a break (soundless period) in which the speech unit 50 temporarily suspends the speech (audio output). The soundless period needs only to be so short that the user U is not distracted from the speech performed by the speech unit 50. With this arrangement, the speech performed by the speech unit 50 can still call for attention from the user U over the speech time period even if the speech time period contains a soundless period. The descriptions given above in (1) to (3) in reference to (a) to (c) of FIG. 4 respectively are similarly applicable to alarm units in the embodiments and variation examples below.

Further Example Timings of Speech and Biological Information Measurement

Portion (b) of FIG. 2 is a timing chart showing further example timings of a speech performed by the speech unit 50 and biological information measurement performed by the measuring unit 51.

The speech time period in the example shown in (b) of FIG. 2 contains a time period (acquisition speech time period) in which the speech unit 50 is controlled to perform a speech (acquisition speech) (e.g., "Measurement starts now.") to let the user U recognize (be aware of) a start of the measurement (biological information acquisition). The acquisition speech time period starts at time tr1 (acquisition speech starting time) and ends at time tr2 (acquisition speech ending time).

The speech unit 50, before the acquisition speech time period, performs a speech (preparatory speech) (e.g., "Measurements are going to be taken of your physical condition. Are you ready?") to urge the user U to be prepared for measurement. When the speech unit 50 is controlled in this manner to perform a preparatory speech prior to an acquisition speech, the user U would not expect the measurement to start until time tr1.

Accordingly, measurement starting time tm1 is set so as to come before tr1 in the example shown in (b) of FIG. 2. The user U is hence in a semi-natural condition and not consciously aware of the measurement during the period from tm1 to tr1. The measuring unit 51 can therefore acquire biological information on the user U in a semi-natural condition in a suitable manner. As described in the foregoing, the measuring unit 51 can acquire biological information on the user U in a semi-natural condition even if the speech unit 50 performs a speech that makes the user U aware of biological information measurement.

With measurement starting time tm1 being set so as to come after tr1, the measuring unit 51 can still acquire biological information on the user U in a semi-natural condition because the user U could be in a semi-natural condition and not consciously aware of the measurement even after an acquisition speech is started, until the user U recognizes either (i) the entire acquisition speech (e.g., "Measurement starts now.") or (ii) a unique word contained in the acquisition speech (e.g., "now" or "measurement").

Therefore, for example, measurement starting time tm1 may be set so as to come after tr1 and before tr2. Under such settings, measurement of the user U may be started before the user U can recognize the entire acquisition speech. Therefore, biological information can be acquired on the user U in a semi-natural condition.

Effects of Biological Information Measuring Instrument 1

Measurement starting time tm1 is set so as to fall in a prescribed range of time defined using speech starting time ta1 as a reference (i.e., so as to satisfy mathematical expression (1)) in the biological information measuring instrument 1 as described above.

Therefore, for example, in the case of (a) of FIG. 4 described above where tm1<ta1, the measuring unit 51 can start biological information measurement before the user U hears the voice output of the speech unit 50. In other words, the measuring unit 51 can start biological information measurement when the user U is still in a natural condition (when the user U is still not consciously aware of the measurement).

Thereafter, as the speech unit 50 starts a speech, the user U goes into a semi-natural condition. The speech performed by the speech unit 50 then calls for attention from the user U in biological information measurement, thereby reducing body movements of the user U in the measurement.

Specifically, as the user U recognizes that the speech unit 50 has started a speech, the user U turns his/her body in the direction of the speech unit 50 and concentrates on listening to the rest of the speech performed by the speech unit 50, which leads to reduced body movements of the user U over the above-described speech time period. Reducing body movements of the user U in the measurement in this manner can in turn reduce errors in biological information measurement. Therefore, biological information can be measured with high precision on the user U in a semi-natural condition.

For example, in the case of (a) of FIG. 2 described above where ta1<tm1, the measuring unit 51 can start biological information measurement after the speech unit 50 starts a speech. In other words, the measuring unit 51 can start biological information measurement within a relatively short period of time after the user U has gone into a semi-natural condition (before the user U becomes consciously aware of the measurement).

Errors in biological information measurement can be reduced in this case similarly to the previous cases, by the speech unit 50 performing a speech calling for attention from the user U in the biological information measurement as described earlier. Therefore, biological information can be measured with high precision on the user U in a semi-natural condition.

Measurement starting time tm1 is set so as to come before speech ending time ta2 (i.e., so as to satisfy mathematical expression (2)) in the biological information measuring instrument 1. Under this setting, the measuring unit 51 can start biological information measurement before the speech unit 50 ends a speech. Therefore, the measuring unit 51 can start biological information measurement while the user U is paying attention. That can more reliably reduce body movements of the user U, which in turn more effectively reduces measurement errors.

Note however that measurement starting time tm1 may be set so as to come after speech ending time ta2. This is because, as an example, if speech ending time ta2 is separated from measurement starting time tm1 by a relatively short length of time, the effects described above can be achieved similarly.

Note also that for the purpose of taking measurements for biological information on the user U in a more natural condition, measurement starting time tm1 is preferably set so as to satisfy tm1<ta1 as in (a) of FIG. 4. This is because under this setting, the measuring unit 51 can start biological information measurement before the speech unit 50 starts a speech calling for attention from the user U as described above.

If the measuring unit 51 performs measurement over a relatively long period (if measurement starting time tm1 is separated from measurement ending time tm2 by a relatively long length of time), measurement starting time tm1 is preferably set in the manner described above. This is because it would be preferable that there be provided a time period in which the user U is not consciously aware of the measurement if the measurement takes a long time. Measurement starting time tm1 is also preferably set in the manner described above when it is preferable that the speech time period be set to be short.

Meanwhile, in view of more effective reduction of measurement errors attributable to body movements of the user U, measurement starting time tm1 is preferably set so as to satisfy ta1<tm1 as shown in, for example, (a) of FIG. 2. This is because biological information measurement can be started while the user U is paying attention to a speech performed by the speech unit 50 as described earlier. In addition, since biological information measurement is performed after the speech unit 50 starts a speech, more stable results of biological information measurement can be obtained.

The measurement control unit 12 may determine, in a suitable manner in accordance with the usage of the biological information measuring instrument 1 with all the above points considered, which one of speech starting time ta1 and measurement starting time tm1 should come before the other.

Alternatively, measurement ending time tm2 may be set so as to satisfy tm2<ta2 as shown in (b) of FIG. 4 in view of even more effective reduction of measurement errors attributable to body movements of the user U. Under this setting, the speech performed by the speech unit 50 can keep calling for attention from the user U in biological information measurement until measurement ending time tm2 is reached. The setting can therefore more reliably reduce body movements of the user U, which can in turn even more effectively reduce measurement errors.

Variation Examples (1) Embodiment 1 has given an imaging device as an example of the measuring unit 51. However, the measuring unit 51, which is capable of contactless measurement of the user U, is not necessarily an imaging device. The measuring unit 51 may be any device that can provide the analysis unit 13 with results of measurement that can be analyzed by the analysis unit 13.

For an example, the measuring unit 51 may be a sensor that measures the vibration of the body surface of the user U in a contactless manner. Specifically, the measuring unit 51 may be a microwave sensor or milliwave radar that measures the vibration of the body surface of the user U by Doppler effect. When this is the case, the analysis unit 13 can acquire biological information such as the heart rate and respiration rate by analyzing the vibration of the body surface of the user U.

(2) As a further alternative, the measuring unit 51 may be a contact-type measuring instrument. That is, the measuring unit 51 may perform contact measurement on the user U. For example, the measuring unit 51 may be a measuring instrument that can be worn by the user U around the clock. Examples of such a measuring instrument include (i) wearable, watch-shaped measuring instruments and (ii) measuring instruments that can be attached to a prescribed body part (e.g., chest) of the user U. The user U would not be consciously aware of the measurement if the user U is constantly wearing the measuring instrument.

The contact-type measuring instrument may alternatively be a sensor shaped like a sheet. Measurements can be taken while the user U is sitting or lying on the sensor, which would not make the user U consciously aware of the measurement.

As described here, even when the measuring unit 51 needs to come in contact with the user U to perform measurement, some measurement methods do not necessarily make the user U consciously aware of the measurement. Therefore, the biological information measuring instrument 1 can acquire biological information on the user U in a semi-natural condition in contact measurement of the user U as well as in contactless measurement of the user U.

(3) Embodiment 1 has given the speech unit 50 as an example of the aural alarm unit. However, the aural alarm unit is by no means limited only to the speech unit 50. In other words, a speech is not the only aural method of calling for attention from the user U.

For example, the aural alarm unit may reproduce a sound effect, music, or any other sound from prescribed audio data for output. The aural alarm unit may be any device so long as the device is capable of performing a prescribed operation (e.g., audio output) that aurally calls for attention from the user U as the above-described alarm operation as described here.

Note however that the aural alarm unit preferably includes the speech unit 50 in view of more effective reduction of measurement errors attributable to body movements of the user U. Upon hearing a speech performed by the speech unit 50, the user U would consciously listen and understand the content of the speech. The speech unit 50 can therefore more effectively call for attention from the user U and hence more effectively reduce body movements of the user U than letting the user U hear a sound such as a sound effect or music.

Embodiment 2

Figure 5:
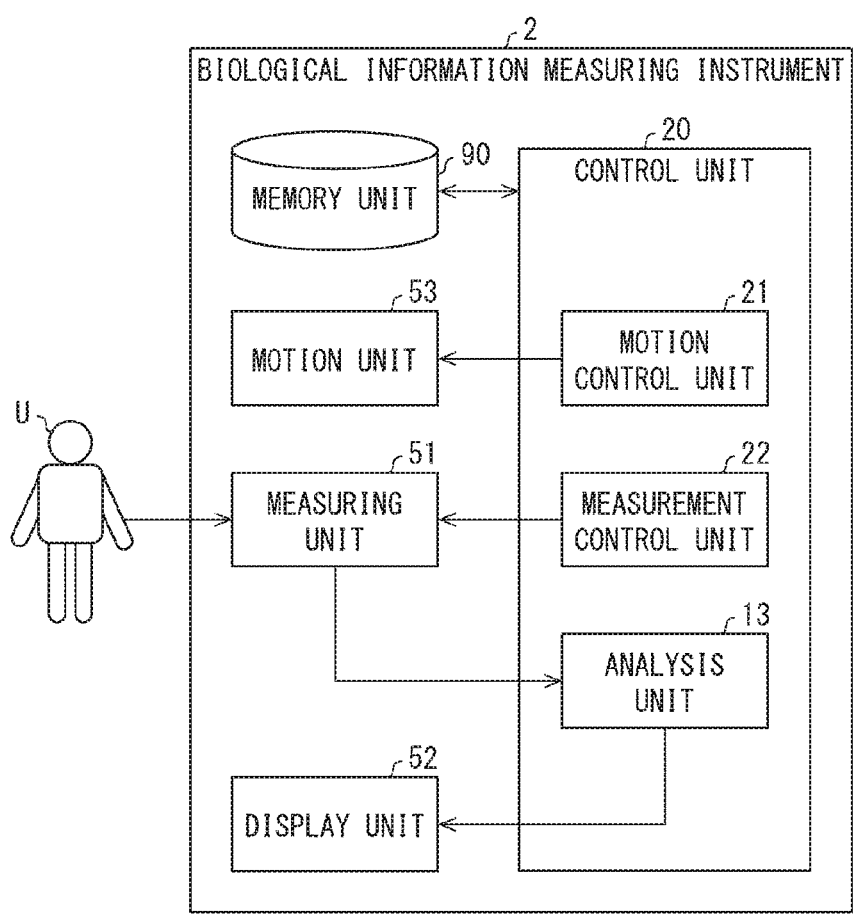
FIG. 5 is a functional block diagram of a configuration of major components of a biological information measuring instrument in accordance with Embodiment 2.
Figure 6:
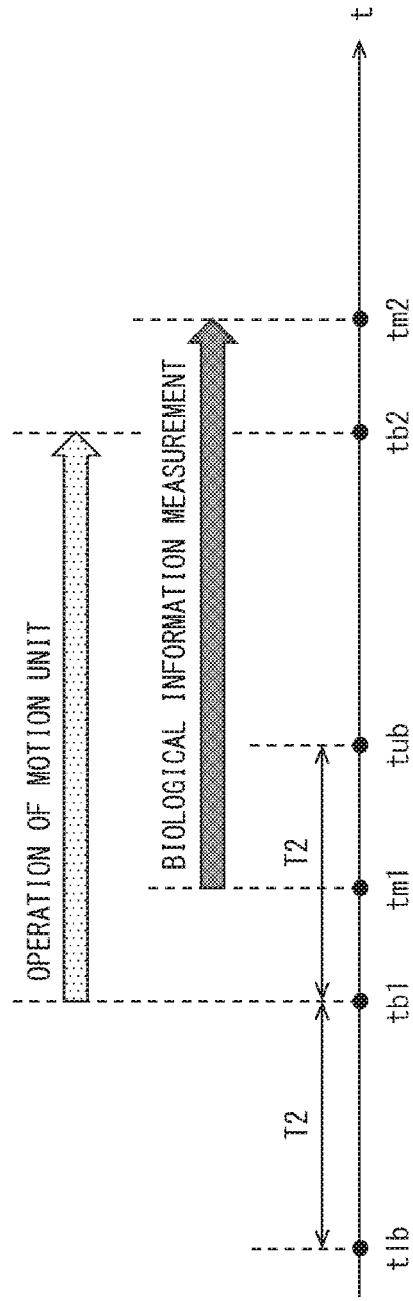
FIG. 6 shows example timings of a motion of a motion unit and biological information measurement in the biological information measuring instrument shown in FIG. 5.
Figure 7:
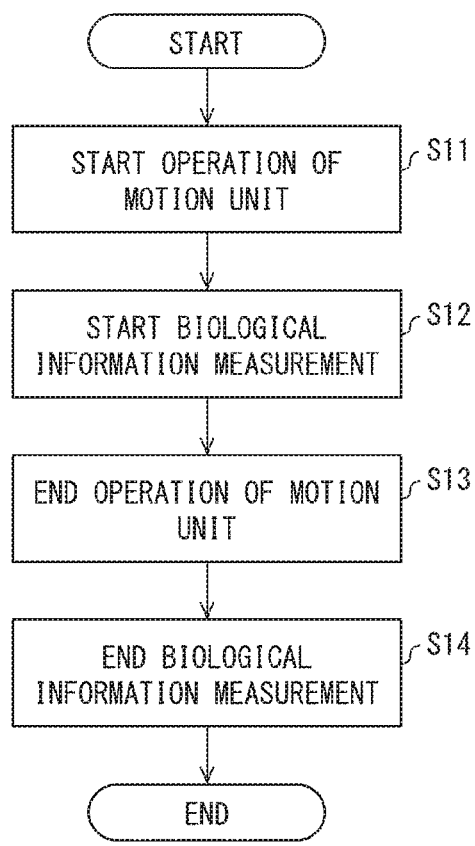
FIG. 7 is a diagram showing an example flow for a process of biological information measurement in the biological information measuring instrument shown in FIG. 5.

The following will describe Embodiment 2 in reference to FIGS. 5 to 7. For convenience of description, members of the present embodiment that have the same function as members of Embodiment 1 are indicated by the same reference numerals, and description thereof is omitted.

FIG. 5 is a functional block diagram of a configuration of major components of a biological information measuring instrument 2 in accordance with Embodiment 2. The biological information measuring instrument 2 differs from the biological information measuring instrument 1 of Embodiment 1 in that (i) the control unit 10 is replaced by a control unit 20 (control device) and (ii) the speech unit 50 is replaced by a motion unit 53 (alarm unit, visual alarm unit). The control unit 20 differs from the control unit 10 in that (i) the measurement control unit 12 is replaced by a measurement control unit 22 and (ii) the speech control unit 11 is replaced by a motion control unit 21.

The motion unit 53 performs a prescribed motion (movement) as the above-described alarm operation. In other words, the motion unit 53 produces a motion calling for attention. The biological information measuring instrument 2 is installed in a robot in Embodiment 2 as an example. The motion unit 53 may be at least a part of a component (housing) of the robot driven by a drive unit (e.g., actuator or servo motor; not shown).

The motion unit 53 plays the role of an alarm unit (visual alarm unit) that visually calls for attention from the user U through its motion in biological information measurement. In other words, the motion unit 53 calls for attention from the user U through a different alarm operation than the speech unit 50 (aural alarm unit) of Embodiment 1.

Similarly to the case of the speech unit 50, the alarm operation performed by the motion unit 53 preferably makes the user U as little aware of the biological information measurement being performed as possible (the alarm operation should to the least possible extent be suggestive of the biological information measurement) in order to take measurements of the user in a semi-natural condition for biological information. As an example, the alarm operation may be a motion that results in the robot making a prescribed gesture. Such an alarm operation would make the user U consciously look at the robot's gesture.

The motion control unit 21 controls the motion of the motion unit 53. As an example, the motion control unit 21 may control the drive unit to control the motion of the motion unit 53. The motion control unit 21 sets start and end timings for the motion of the motion unit 53, which is described more specifically in the following.

Example Timings of Motion of Motion Unit and Biological Information Measurement

FIG. 6 is a timing chart showing example timings of a motion of the motion unit 53 and biological information measurement performed by the measuring unit 51 in the biological information measuring instrument 2. Referring to FIG. 6, the motion control unit 21 sets (i) a starting time for a motion of the motion unit 53 to time tb1 and (ii) an ending time for that motion of the motion unit 53 to time tb2. In the rest of the description, time tb1 may be referred to as a motion starting time (alarm starting time, visual alarm starting time), and time tb2 may be referred to as a motion ending time (alarm ending time, visual alarm ending time).

The measurement control unit 22 further sets measurement starting time tm1 so as to fall in a prescribed range of time defined using motion starting time tb1 as a reference and sets measurement starting time tm1 so as to come before motion ending time tb2. Specifically, as shown in FIG. 6, the measurement control unit 22 sets measurement starting time tm1 so as to satisfy mathematical expressions (3) and (4).

$$tlb \leq tm1 \leq tub \quad (3)$$

$$tm1 < tb2 \quad (4)$$

Note that $tlb=tb1-\beta1$ in mathematical expression (3), where tlb may be referred to as the earliest motion starting reference time. Note also that $tub=tb1+\beta2$ in mathematical expression (3), where tub may be referred to as the last motion starting reference time.

Similarly to mathematical expression (2) of Embodiment 1 described above, satisfying mathematical expression (4) of Embodiment 2 is not an essential condition in the biological information measuring instrument in an aspect of the present disclosure. Embodiment 2 illustrates, as an example, measurement starting time tm1 being set so as to satisfy both mathematical expressions (3) and (4).

Similarly to the values of $\alpha1$ and $\alpha2$ in the above-described mathematical expression (1), the values of $\beta1$ and $\beta2$ in mathematical expression (3) may be predetermined in the biological information measuring instrument 2. The measurement control unit 22 sets tlb and tub using the predetermined values of $\beta1$ and $\beta2$ in reference to motion starting time tb1. The value of $\beta2$ needs to be set by taking mathematical expression (4) into consideration so as to satisfy tub<tb2.

Embodiment 2 illustrates an example where $\beta1=\beta2=T2$ for the purpose of simplicity. In other words, the measurement control unit 22 sets measurement starting time tm1 so as to fall in a temporal range $tb1\pm T2$ in Embodiment 2.

Measurement starting time tm1 is set so as to satisfy tb1<tm1, and measurement ending time tm2 is set so as to satisfy tb2<tm2, in the example shown in FIG. 6. In other words, in the biological information measuring instrument 2, (i) the motion unit 53 starts a motion before the measuring unit 51 starts measurement, and (ii) the motion unit 53 ends the motion before the measuring unit 51 ends the measurement, as an example.

Similarly to Embodiment 1 described above, the motion unit 53 and the measuring unit 51 do not necessarily perform a motion and biological information measurement respectively at the timings given in the example shown in FIG. 6. Measurement starting time tm1 in Embodiment 2 needs only to be set so as to satisfy mathematical expressions (3) and (4).

Flow of Process of Biological Information Measurement in Biological Information Measuring Instrument 2

FIG. 7 is a flow chart of an example flow of a process S11 to S14 (control steps) of biological information measurement in the biological information measuring instrument 2. FIG. 7 shows, as an example, a flow of a process where measurement starting time tm1 and measurement ending time tm2 are set so as to satisfy tb1<tm1 and tb2<tm2 as shown in FIG. 6.

S12 and S14 are analogous respectively to S2 and S4 described earlier, and description thereof is omitted. Referring to FIG. 7, the motion control unit 21 controls the motion unit 53 to start a motion at motion starting time tb1 (S11). Subsequent to S12, the motion control unit 21 controls the motion unit 53 to end the motion at motion ending time tb2 (S13).

As described in the foregoing, the motion unit 53 (visual alarm unit) replaces the speech unit 50 (aural alarm unit) in the biological information measuring instrument 2, to call for attention from the user U. The biological information measuring instrument 2 achieves effects similar to those described in Embodiment 1.

Variation Examples (1) Embodiment 2 has given the motion unit 53 as an example of the visual alarm unit. However, the visual alarm unit is by no means limited only to the motion unit 53. In other words, a mechanical component producing a motion is not the only visual method of calling for attention from the user U. The visual alarm unit may be any device so long as the device is capable of performing a prescribed motion that visually calls for attention from the user U as the above-described alarm operation.

For example, the biological information measuring instrument 2 may include a light source such as LEDs (light-emitting diodes) to use the light source as a visual alarm unit. In such a case, the light source may flash, thereby visually calling for attention from the user U. Alternatively, the display unit 52 may be used as a visual alarm unit. When this is the case, the display unit 52 may display a prescribed moving image, thereby visually calling for attention from the user U.

(2) The alarm unit, in an aspect of the present disclosure, is by no means limited only to the aural alarm unit or the visual alarm unit. For example, the alarm unit may be an olfactory alarm unit olfactorily calling for attention from the user U. As an example, the biological information measuring instrument 2 may include an aroma generator (odor generator) that produces a gas that has a prescribed odor. When this is the case, the aroma generator may be used as an olfactory alarm unit that performs an alarm operation (generates odor).

As described in the foregoing, the alarm unit, in an aspect of the present disclosure, may be any device so long as the device is capable of performing an alarm operation (alarm) calling for attention from the user U. The alarm operation may also be any operation. The specific alarm units described above (e.g., aural alarm unit, visual alarm unit, and olfactory alarm unit) may be combined to constitute a single alarm unit. In other words, the alarm unit, in an aspect of the present disclosure, may include at least one of the alarm units described above. An example will be described in Embodiment 3 next.

Embodiment 3

Figure 8:
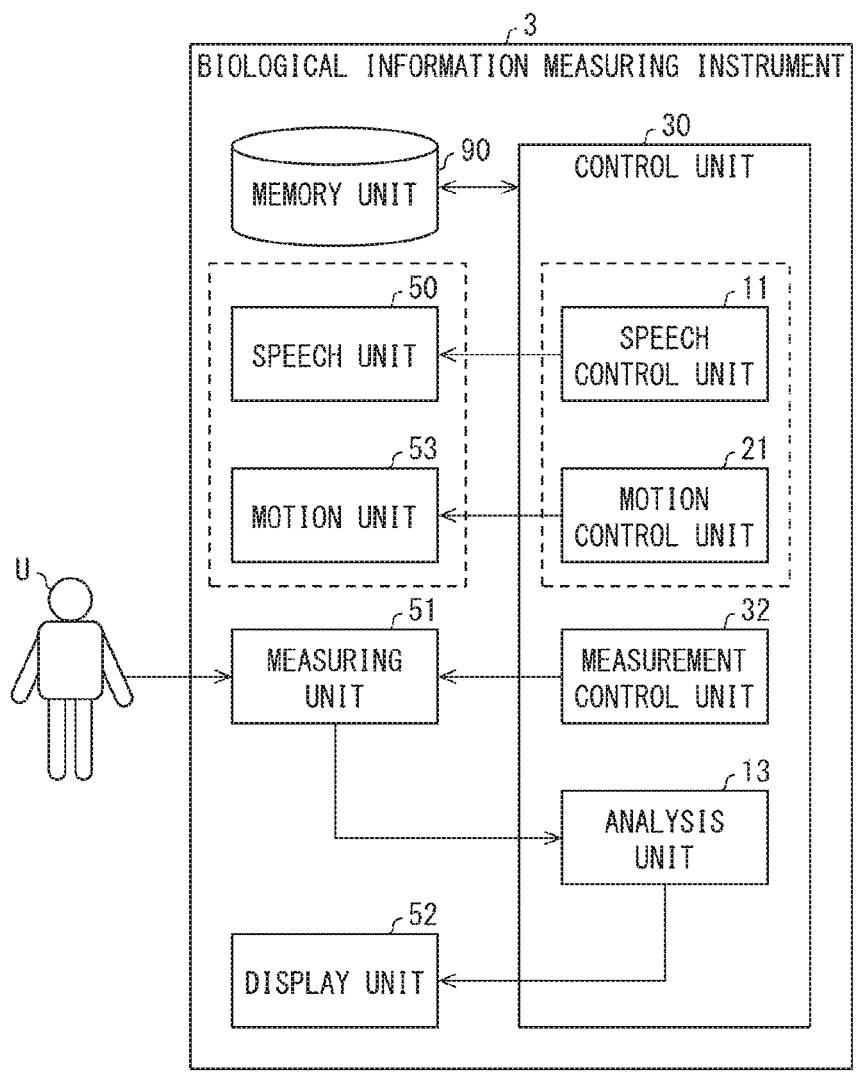
FIG. 8 is a functional block diagram of a configuration of major components of a biological information measuring instrument in accordance with Embodiment 3.
Figure 9:
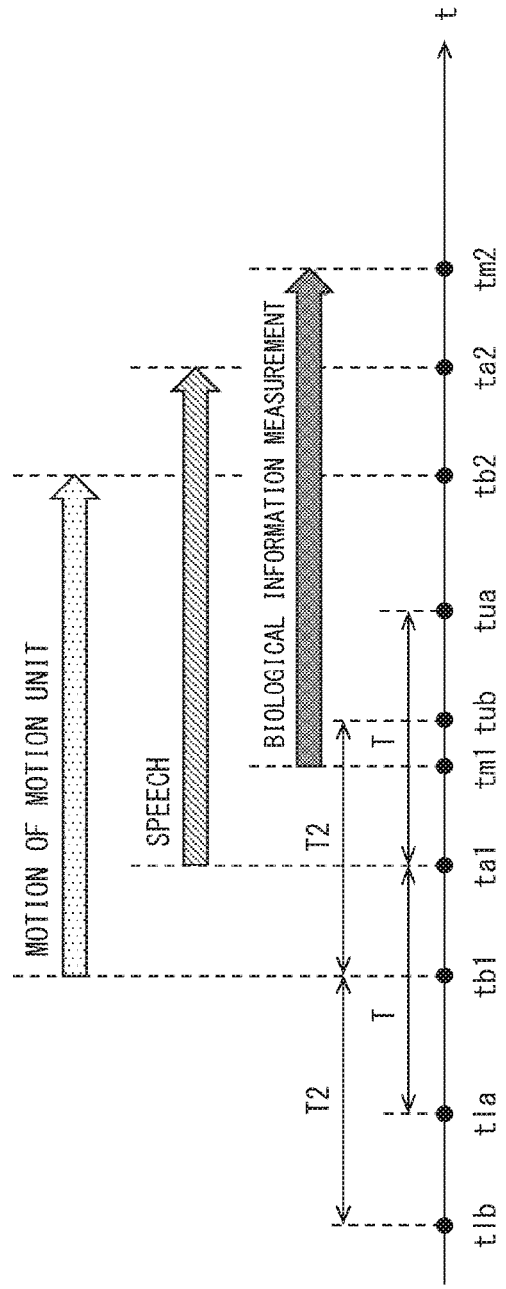
FIG. 9 shows example timings of a motion of a motion unit, a speech, and, biological information measurement in the biological information measuring instrument shown in FIG. 8.

The following will describe Embodiment 3 in reference to FIGS. 8 to 9. FIG. 8 is a functional block diagram of a configuration of major components of a biological information measuring instrument 3 in accordance with Embodiment 3. The biological information measuring instrument 3 differs from the biological information measuring instrument 1 of Embodiment 1 in that (i) the control unit 10 is replaced by a control unit 30 (control device) and (ii) the motion unit 53 of Embodiment 2 is added.

The control unit 30 differs from the control unit 10 in that (i) the measurement control unit 12 is replaced by a measurement control unit 32 and (ii) the motion control unit 21 of Embodiment 2 is added. The biological information measuring instrument 3 is a combination of the configuration of the biological information measuring instrument 1 and the configuration of the biological information measuring instrument 2 as described here. In other words, the speech unit 50 and the motion unit 53 are combined in the biological information measuring instrument 3 to provide an alarm unit.

Example Timings of Motion of Motion Unit, Speech, and Biological Information Measurement FIG. 9 is a timing chart showing example timings of a motion of the motion unit 53, a speech performed by the speech unit 50, and biological information measurement performed by the measuring unit 51 in the biological information measuring instrument 3. The measurement control unit 32 sets measurement starting time tm1 so as to satisfy mathematical expressions (1) to (4) described earlier.

Measurement starting time tm1 is set so as to satisfy tb1<ta1<tm1, and measurement ending time tm2 is set so as to satisfy tb2<ta2<tm2, in the example shown in FIG. 9. In other words, in the biological information measuring instrument 3, (i) the motion unit 53, the speech unit 50, and the measuring unit 51 start operating in this sequence and (ii) the motion unit 53, the speech unit 50, and the measuring unit 51 end operating in this sequence, as an example.

The motion unit 53, the speech unit 50, and the measuring unit 51 do not necessarily perform a motion, a speech, and biological information measurement respectively at the timings given in the example shown in FIG. 9 as described above. Measurement starting time tm1 in Embodiment 3 needs only to be set so as to satisfy mathematical expressions (1) to (4).

Motion starting time tb1 in the example shown in FIG. 9 is the earliest timing for the alarm unit of Embodiment 3, which is a combination of the speech unit 50 and the motion unit 53, to start an alarm operation. Therefore, motion starting time tb1 may be regarded as an alarm starting time for the alarm unit. Meanwhile, speech ending time ta2 is the last timing for the alarm unit to end an alarm operation. Therefore, speech ending time ta2 may be regarded as an alarm ending time for the alarm unit.

As described in the foregoing, the alarm unit, which is a combination of the speech unit 50 and the motion unit 53, aurally and visually calls for attention from the user U in the biological information measuring instrument 3. The alarm unit can thereby more reliably call for attention from the user U.

Relationship Between Speech Starting Time ta1 and Motion Starting Time tb1

In the example shown in FIG. 9 described above, tb1<ta1 so that the motion unit 53 can start a motion before the speech unit 50 starts a speech. Accordingly, the motion unit 53 can first perform a motion to visually call for attention from the user, so that the user U can move toward the biological information measuring instrument 3. Then, the speech unit 50 performs a speech, calling for more attention from the user U.

As an example, the user U may find it difficult to immediately identify the location and direction of the source of the audio speech in some forms of speech performed by the speech unit 50. It would be preferable that tb1<ta1 as in the example shown in FIG. 9 in such a situation.

Alternatively, the setting, ta1<tb1, may be used, so that the speech unit 50 can perform a speech prior to a motion of the motion unit 53. Accordingly, the user U would visually search his/her surroundings in response to the speech unit 50 starting to perform a speech. Then, the motion unit 53 performs a motion, more reliably causing the user U to move toward the biological information measuring instrument 3.

Embodiment 4

Figure 10:
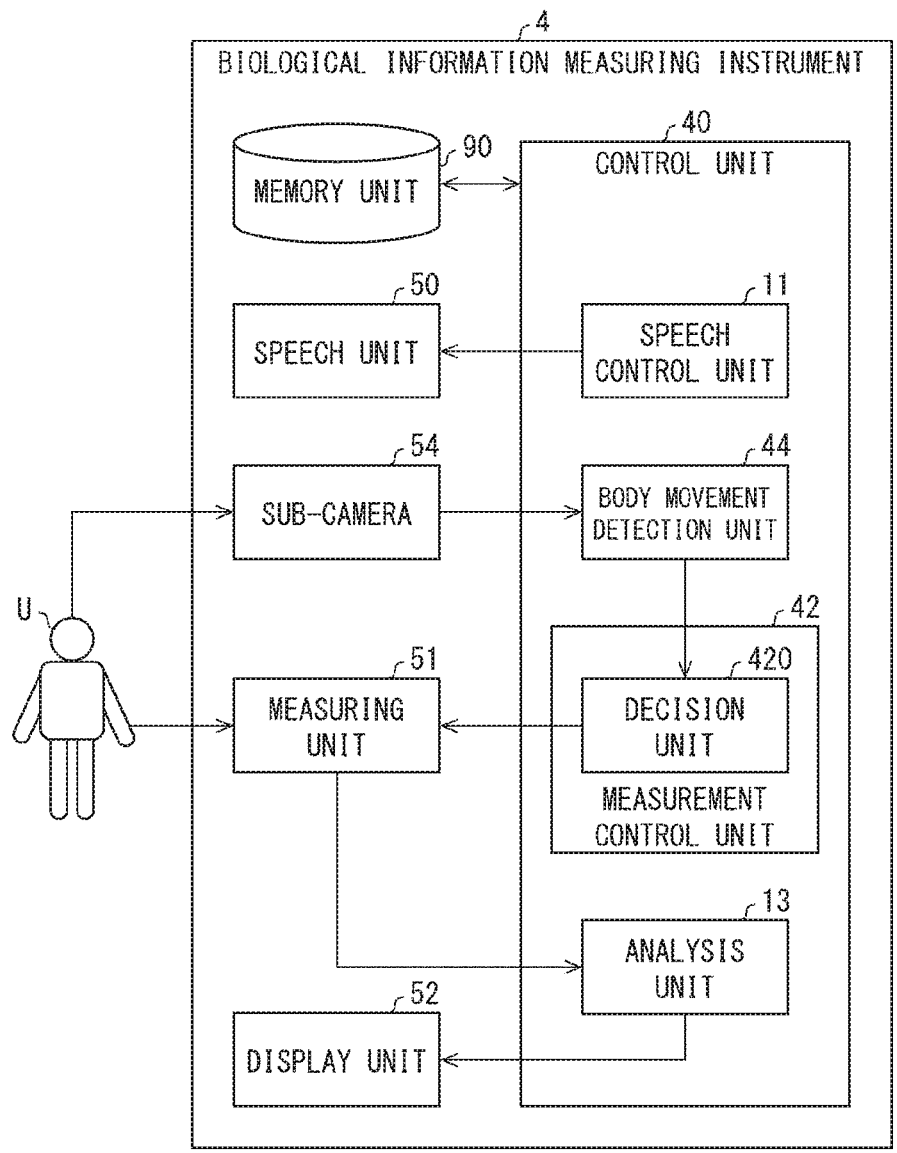
FIG. 10 is a functional block diagram of a configuration of major components of a biological information measuring instrument in accordance with Embodiment 4.

The following will describe Embodiment 4 in reference to FIGS. 9 to 10. FIG. 9 is a functional block diagram of a configuration of major components of a biological information measuring instrument 4 in accordance with Embodiment 4. The biological information measuring instrument 4 differs from the biological information measuring instrument 1 of Embodiment 1 in that (i) the control unit 10 is replaced by a control unit 40 (control device) and (ii) a sub-camera 54 (body movement acquisition unit) is added.

The control unit 40 differs from the control unit 10 in that (i) the measurement control unit 12 is replaced by a measurement control unit 42 and (ii) a body movement detection unit 44 (body movement acquisition unit) is added. The measurement control unit 42 differs from the measurement control unit 12 that a decision unit 420 is added.

The sub-camera 54 is an imaging device that is provided separately from the measuring unit 51 (imaging device). The sub-camera 54 captures images of the entire body of the user U to obtain a moving image without restraining the movement of the user U. The sub-camera 54 supplies the image as a result of detection to the body movement detection unit 44. For convenience, the capturing of a moving image by the sub-camera 54 may be referred to as the "detection of a body movement." The control unit 40 controls the operation of the sub-camera 54 (more specifically, the start and end timings of image capturing). For example, the measurement control unit 42 may control the operation of the sub-camera 54.

The body movement detection unit 44 analyzes the result of detection (moving image) acquired from the sub-camera 54 to detect (calculate) the magnitude of a body movement of the user U. The body movement detection unit 44 and the sub-camera 54 may be collectively called a body movement acquisition unit (i.e., a functional unit that acquires the magnitude of a body movement of the user U). Embodiment 4 illustrates, as an example, the body movement detection unit 44 and the sub-camera 54 being provided as separate functional units. Alternatively, the body movement acquisition unit may be provided as an integrated single functional unit as will be described later.

As an example, the body movement detection unit 44 may analyze the moving image by a known movement detection algorithm to calculate a physical quantity that represents the magnitude of a body movement of the user U. Examples of the physical quantity that represents the magnitude of a body movement of the user U include displacement, velocity, acceleration, and angular velocity. Embodiment 4 illustrates, as an example, the physical quantity that represents the magnitude of a body movement of the user U being a displacement of the user U. The displacement of the user U detected by the body movement detection unit 44 will be denoted by Du in the following.

The decision unit 420 acquires the displacement Du from the body movement detection unit 44 and compares the magnitudes of the displacement Du and a prescribed threshold DT. In other words, the decision unit 420 determines whether or not Du<DT. The decision unit 420 determines, in this manner, whether or not the magnitude of a body movement of the user U is smaller than a prescribed magnitude. The threshold DT is a physical quantity representing a prescribed magnitude of a body movement of the user and may be set to a suitable value on the decision unit 420.

The decision unit 420 allows the measuring unit 51 to perform measurement if Du<DT (if the magnitude of a body movement of the user U is smaller than a prescribed magnitude; this condition may be referred to as a measurement allowing condition in the following). In other words, if the measurement allowing condition is satisfied, the decision unit 420 allows the biological information acquisition unit to acquire biological information.

On the other hand, the decision unit 420 does not allow the measuring unit 51 to perform measurement if Du≥DT (if the magnitude of a body movement of the user U is greater than or equal to a prescribed magnitude; this condition may be referred to as a measurement forbidding condition in the following). In other words, if the measurement forbidding condition is satisfied, the decision unit 420 does not allow the biological information acquisition unit to acquire biological information. The following will describe specific examples of the operation of the decision unit 420.

Figure 11:
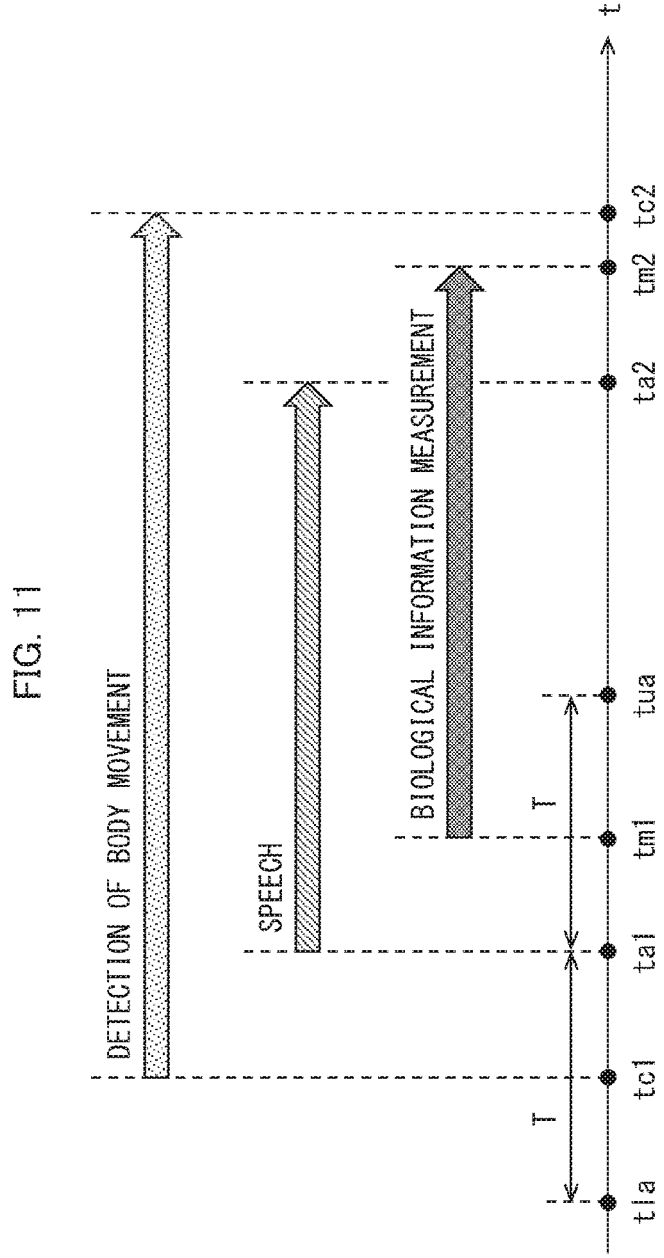
FIG. 11 shows example timings of a detection of a body movement, a speech, and biological information measurement in the biological information measuring instrument shown in FIG. 10.

Example Timings of Detection of Body Movement, Speech, and Biological Information Measurement FIG. 11 is a timing chart showing example timings of detection (capturing of a moving image) of a body movement by the sub-camera 54, a speech performed by the speech unit 50, and biological information measurement performed by the measuring unit 51 in the biological information measuring instrument 4.

Referring to FIG. 11, the measurement control unit 42 sets (i) a starting time for detection of a body movement by the sub-camera 54 to time tc1 and (ii) an ending time for that detection of a body movement by the sub-camera 54 to time tc2. In the rest of the description, time tc1 may be referred to as a body movement detection staring time, and time tc2 may be referred to as a body movement detection ending time.

Body movement detection staring time tc1 is set so as to satisfy tc1<ta1<tm1, and body movement detection ending time tc2 is set so as to satisfy ta2<tm2<tc2, in the example shown in FIG. 11. In other words, in the biological information measuring instrument 4, (i) the sub-camera 54 starts detection of a body movement before speech starting time ta1 and measurement starting time tm1 and (ii) the sub-camera 54 ends the detection of a body movement after speech ending time ta2 and measurement ending time tm2, as an example. The following will describe an example operation of the biological information measuring instrument 4 in the example shown in FIG. 11.

The body movement detection unit 44 calculates the displacement Du of the user U over a time period (body movement detection period), tc1≤t≤tc2, on the basis of the moving image acquired from the sub-camera 54. The decision unit 420 then acquires the displacement Du from the body movement detection unit 44 over the body movement detection period, to determine whether a measurement allowing condition (Du<DT) is satisfied or a measurement forbidding condition (Du≥DT) is satisfied.

The decision unit 420 allows the measuring unit 51 to perform measurement if the measurement allowing condition is satisfied as described earlier. For example, if the measurement allowing condition is satisfied at measurement starting time tm1, the decision unit 420 causes the measuring unit 51 to start measurement. Thereafter, if the measurement allowing condition is satisfied in a time period tm1<t<tm2, the decision unit 420 causes the measuring unit 51 to continue measurement. The decision unit 420 then causes the measuring unit 51 to end the measurement at measurement ending time tm2.

On the other hand, if the measurement forbidding condition is satisfied, the decision unit 420 does not allow the measuring unit 51 to perform measurement. For example, if the measurement forbidding condition is satisfied at measurement starting time tm1, the decision unit 420 does not allow the measuring unit 51 to perform measurement (the measuring unit 51 continues to suspend the operation thereof). In this example, the decision unit 420 causes the measuring unit 51 to not start measurement until time t at which the measurement allowing condition is satisfied for the first time.

Even if the measuring unit 51 starts measurement at measurement starting time tm1 (e.g., if the measurement allowing condition is satisfied at measurement starting time tm1), the decision unit 420 suspends the operation (measurement) of the measuring unit 51 upon the measurement forbidding condition being satisfied in a time period tm1<t<tm2, until the measurement allowing condition is satisfied again.

The sub-camera 54, the speech unit 50, and the measuring unit 51 in the biological information measuring instrument 4 do not necessarily perform detection of a body movement, a speech, and biological information measurement respectively at the timings given in the example shown in FIG. 11. For example, body movement detection staring time tc1 may be set so as to come after either one or both of speech starting time ta1 and measurement starting time tm1. The timings may be set in any appropriate manner so long as measurement starting time tm1 is set so as to satisfy mathematical expressions (1) and (2), as described earlier.

Effects of Biological Information Measuring Instrument 4

The biological information measuring instrument 4 allows the measuring unit 51 to perform measurement only when the measurement allowing condition is satisfied (i.e., when the user U is making no body movement at all or making a relatively small body movement). On the other hand, when the measurement forbidding condition is satisfied (i.e., when the user U is making a relatively large body movement), the biological information measuring instrument 4 does not allow the measuring unit 51 to perform measurement.

In other words, the biological information measuring instrument 4 allows the biological information acquisition unit to acquire biological information only when the body movement of the user U is causing no or relatively small measurement errors. In other words, biological information can be acquired selectively by eliminating relatively large measurement errors, which enables more precise measurement of biological information.

Variation Examples

Embodiment 4 has so far described an example where the body movement detection unit 44 analyzes the moving image captured by the sub-camera 54 to detect (calculate) a physical quantity that represents the magnitude of a body movement of the user U. This is however not the only possible implementation of the invention. The magnitude of a body movement of the user U may be detected by any other method. For example, the body movement acquisition unit may be a sensor that detects the physical quantity.

The sensor used as the body movement acquisition unit may be, for example, a displacement sensor, a velocity sensor, an acceleration sensor, or an angular velocity sensor. The sensor may be either a contact-type sensor or a contactless sensor. It is however preferable that a contactless sensor be used so that the user U is not consciously aware of the measurement.

Software Implementation

The control blocks of the biological information measuring instruments 1 to 4 (particularly, the control units 10 to 40) may be implemented by logic circuits (hardware) fabricated, for example, in the form of an integrated circuit (IC chip) and may be implemented by software executed by a CPU (central processing unit).

In the latter form of implementation, the biological information measuring instruments 1 to 4 include among others a CPU that executes instructions from programs or software by which various functions are implemented, a ROM (read-only memory) or like storage device (referred to as a "storage medium") containing the programs and various data in a computer-readable (or CPU-readable) format, and a RAM (random access memory) into which the programs are loaded. The computer (or CPU) then retrieves and executes the programs contained in the storage medium, thereby achieving the object of an aspect of the present disclosure. The storage medium may be a "non-transient, tangible medium" such as a tape, a disc, a card, a semiconductor memory, or programmable logic circuitry. The programs may be fed to the computer via any transmission medium (e.g., over a communications network or by broadcasting waves) that can transmit the programs. The present disclosure, in an aspect thereof, encompasses data signals on a carrier wave that are generated during electronic transmission of the programs.

General Description

The present disclosure, in aspect 1 thereof, is directed to a biological information measuring instrument (1) including: a biological information acquisition unit (measuring unit 51, analysis unit 13) configured to measure a living body (user U) to acquire biological information on the living body; an alarm unit (e.g., speech unit 50) configured to produce an alarm calling for attention from the living body; and a control unit (e.g., measurement control unit 12, speech control unit 11) configured to control the biological information acquisition unit and the alarm unit, wherein: the alarm unit starts the alarm at an alarm starting time (e.g., speech starting time ta1) and ends the alarm at an alarm ending time (e.g., speech ending time ta2); the biological information acquisition unit starts acquisition of the biological information at an acquisition starting time (measurement starting time tm1); and the control unit sets the acquisition starting time so as to fall in a prescribed range of time defined using the alarm starting time as a reference.

With this arrangement, the biological information acquisition unit can start acquisition (measurement) of biological information either (i) before the living body pays attention to the alarm produced by the alarm unit or (ii) within a relatively short period of time after the living body pays attention to the alarm, as described earlier. In other words, the biological information acquisition unit can start acquiring biological information when the living body is still in a natural condition or in a semi-natural condition.

In addition, the alarm calls for attention from the living body in acquiring biological information, thereby reducing body movements of the living body. Measurement errors are therefore reduced that are attributable to body movements of the living body, which also improves the precision of the measurement of biological information of the living body in a semi-natural condition. High precision measurement hence becomes possible of the living body to acquire biological information. The measurement of the living body may be performed either in a contactless manner or in contact with the living body.

In aspect 2 of the present disclosure, the biological information measuring instrument of aspect 1 may be configured such that the biological information acquisition unit measures the living body in a contactless manner to acquire the biological information.

This arrangement facilitates the measurement of biological information of the living body in a semi-natural condition.

In aspect 3 of the present disclosure, the biological information measuring instrument of aspect 1 or 2 may be configured such that the alarm unit includes an aural alarm unit (e.g., speech unit 50) configured to produce, as the alarm, an alarm aurally calling for attention from the living body.

With this arrangement, the biological information measuring instrument can aurally call for attention from the living body.

In aspect 4 of the present disclosure, the biological information measuring instrument of aspect 3 may be configured such that the aural alarm unit includes a speech unit (50) configured to produce a speech as the alarm.

With this arrangement, the biological information measuring instrument can more effectively call for attention from the living body through the speech and hence more effectively reduce body movements of the living body.

In aspect 5 of the present disclosure, the biological information measuring instrument of aspect 4 may be configured such that: the speech unit starts at an acquisition speech starting time (tr1) a speech by which the living body recognizes a start of the acquisition of the biological information; and the acquisition starting time comes before the acquisition speech starting time.

With this arrangement, the biological information measuring instrument can measure biological information of the user U in a semi-natural condition in a suitable manner even if the speech unit performs a speech that makes the living body aware of the biological information measurement.

In aspect 6 of the present disclosure, the biological information measuring instrument of any one of aspects 1 to 5 may be configured such that the alarm unit includes a visual alarm unit (e.g., motion unit 53) configured to produce, as the alarm, an alarm visually calling for attention from the living body.

With this arrangement, the biological information measuring instrument can visually call for attention from the living body.

In aspect 7 of the present disclosure, the biological information measuring instrument of aspect 6 may be configured such that the visual alarm unit includes a motion unit (53) configured to perform a motion calling for attention.

With this arrangement, the biological information measuring instrument can visually call for attention from the living body through the motion.

In aspect 8 of the present disclosure, the biological information measuring instrument of any one of aspects 1 to 7 may be configured so as to further include a body movement acquisition unit (body movement detection unit 44, sub-camera 54) configured to acquire a magnitude of a body movement of the living body, wherein if the magnitude of the body movement acquired by the body movement acquisition unit is smaller than a prescribed magnitude, the control unit (decision unit 420) allows the biological information acquisition unit to acquire the biological information.

According to this arrangement, the biological information acquisition unit acquires biological information only if the body movement of the living body is relatively small (i.e., if the body movement is causing no or relatively small measurement errors). That improves the precision of the measurement of biological information.

In aspect 9 of the present disclosure, the biological information measuring instrument of any one of aspects 1 to 8 may be configured such that the acquisition starting time comes before the alarm ending time.

With this arrangement, the biological information measuring instrument can start acquiring biological information while calling for attention from the living body through the alarm, which more effectively reduce body movements of the living body.

In aspect 10 of the present disclosure, the biological information measuring instrument of any one of aspects 1 to 9 may be configured such that the acquisition starting time comes before the alarm starting time.

With this arrangement, the biological information measuring instrument can start acquiring biological information before calling for attention from the living body through the alarm, which enables acquisition of biological information from the living body in a more natural condition.

In aspect 11 of the present disclosure, the biological information measuring instrument of any one of aspects 1 to 9 may be configured such that the acquisition starting time comes after the alarm starting time.

With this arrangement, the biological information measuring instrument can start acquiring biological information while calling for attention from the living body through the alarm, which more effectively reduce body movements of the living body.

In aspect 12 of the present disclosure, the biological information measuring instrument of any one of aspects 1 to 11 may be configured such that: the biological information acquisition unit ends the acquisition of the biological information at an acquisition ending time (measurement ending time tm2); and the control unit sets the acquisition ending time so as to come before the alarm ending time.

With this arrangement, the biological information measuring instrument can call for attention from the living body through the alarm until the measurement ending time, which more effectively reduces body movements of the living body.

In aspect 13 of the present disclosure, the biological information measuring instrument of any one of aspects 1 to 12 may be configured such that the control unit controls the alarm unit to produce the alarm intermittently from the alarm starting time to the alarm ending time.

With this arrangement, the biological information measuring instrument can call for attention from the living body through the intermittent alarm produced by the alarm unit.

The present disclosure, in aspect 14 thereof, is directed to a method of controlling a biological information measuring instrument including: a biological information acquisition unit configured to measure a living body to acquire biological information on the living body; and an alarm unit configured to produce an alarm calling for attention from the living body, the method including the control step of controlling the biological information acquisition unit and the alarm unit, wherein: the alarm unit starts the alarm at an alarm starting time and ends the alarm at an alarm ending time; the biological information acquisition unit starts acquisition of the biological information at an acquisition starting time; and the control step includes setting the acquisition starting time so as to fall in a prescribed range of time defined using the alarm starting time as a reference.

This arrangement achieves advantages similar to those achieved by a biological information measuring instrument of an aspect of the present disclosure.

The present disclosure, in aspect 15 thereof, is directed to a control device (control unit 10) that controls a biological information measuring instrument including: a biological information acquisition unit configured to measure a living body to acquire biological information on the living body; and an alarm unit configured to produce an alarm calling for attention from the living body, the control device including a control unit configured to control the biological information acquisition unit and the alarm unit, wherein: the alarm unit starts the alarm at an alarm starting time and ends the alarm at an alarm ending time; the biological information acquisition unit starts acquisition of the biological information at an acquisition starting time; and the control unit sets the acquisition starting time so as to fall in a prescribed range of time defined using the alarm starting time as a reference.

This arrangement achieves advantages similar to those achieved by a biological information measuring instrument of an aspect of the present disclosure.

The control device of any aspect of the present disclosure may be implemented on a computer, in which case that aspect of the present disclosure encompasses a control program, for controlling the control device, which when run on a computer causes the computer to operate as the various units (software elements) of the control device and also encompasses a computer-readable storage medium containing the control program.

Additional Remarks

Each aspect of the present disclosure is not limited to the description of the embodiments above and may be altered within the scope of the claims. Embodiments based on a proper combination of technical means disclosed in different embodiments are encompassed in the technical scope of that aspect of the present disclosure. Furthermore, a new technological feature may be created by combining different technological means disclosed in the embodiments.

Another Expression of Aspects of Present Disclosure

Aspects of the present disclosure may be delineated as in the following.

The present disclosure, in one aspect thereof, is directed to a biological information measuring instrument including: a measuring unit configured to measure biological information of a user; and a speech unit configured to perform a speech, wherein the measuring unit starts measuring the biological information of the user either a prescribed length of time before the speech unit performs a speech calling for attention from the user or while the speech unit is performing the speech.

The biological information measuring instrument of another aspect of the present disclosure further includes a motion unit configured to generate a motion, wherein the measuring unit starts measuring the biological information of the user either a prescribed length of time before the motion unit generates a motion calling for attention from the user or while the motion unit is generating the motion.

The biological information measuring instrument of a further aspect of the present disclosure further includes a body movement detection unit configured to detect a body movement of the user, wherein if the body movement detected by the body movement detection unit has a magnitude smaller than a prescribed magnitude, the measuring unit starts measuring the biological information of the user.

The biological information measuring instrument of still another aspect of the present disclosure further includes an image processing unit configured to identify a face region of the user, wherein the measuring unit measures the biological information in the face region identified by the image processing unit.

In the biological information measuring instrument of yet another aspect of the present disclosure, the biological information is information on at least one of heart rate, blood pressure, and stress level.

CROSS-REFERENCE TO RELATED APPLICATIONS

The present application claims the benefit of priority to Japanese Patent Application, Tokugan, No. 2016-217488, filed on Nov. 7, 2016, the entire contents of which are incorporated herein by reference.

REFERENCE SIGNS LIST 1, 2, 3, 4 Biological Information Measuring Instrument
10, 20, 30, 40 Control Unit (Control Device)
11 Speech Control Unit (Control Unit)
12, 22, 32, 42 Measurement Control Unit (Control Unit)
13 Analysis Unit (Biological Information Acquisition Unit)
21 Motion Control Unit (Control Unit)
44 Body Movement Detection Unit (Body Movement Acquisition Unit)
420 Decision Unit (Control Unit)
50 Speech Unit (Alarm Unit, Aural Alarm Unit)
51 Measuring Unit (Biological Information Acquisition Unit)
53 Motion Unit (Alarm Unit, Visual Alarm Unit)
54 Sub-camera (Body Movement Acquisition Unit)
U User (Living Body)
ta1 Speech Starting Time (Alarm Starting Time)
ta2 Speech Ending Time (Alarm Ending Time)
tb1 Motion Starting Time (Alarm Starting Time)
tb2 Motion Ending Time (Alarm Ending Time)
tm1 Measurement Starting Time (Acquisition Starting Time)
tm2 Measurement Ending Time (Acquisition Ending Time)
tr1 Acquisition Speech Starting Time
tr2 Acquisition Speech Ending Time

The invention claimed is:

1. A biological information measuring instrument comprising:
a biological information acquisition unit configured to measure a living body to acquire biological information on the living body;
an alarm unit configured to produce an alarm for reducing body movements of the living body; and
a control unit configured to control the biological information acquisition unit and the alarm unit,
wherein:
the alarm unit starts the alarm at an alarm starting time and ends the alarm at an alarm ending time;
the biological information acquisition unit starts acquisition of the biological information at an acquisition starting time;
the control unit sets the acquisition starting time so as to fall in a prescribed range of time defined using the alarm starting time as a reference;
the alarm unit includes a visual alarm unit configured to perform, as the alarm, an alarm operation visually calling for attention from the living body; and
the alarm operation is an operation that calls for attention to the alarm operation without suggesting the acquisition of the biological information to the living body.

2. The biological information measuring instrument according to claim 1, wherein the biological information acquisition unit measures the living body in a contactless manner to acquire the biological information.

3. The biological information measuring instrument according to claim 2, wherein the alarm unit includes an aural alarm unit configured to produce, as the alarm, an alarm aurally calling for attention from the living body.

4. The biological information measuring instrument according to claim 1, wherein the alarm unit includes an aural alarm unit configured to produce, as the alarm, an alarm aurally calling for attention from the living body.

5. The biological information measuring instrument according to claim 4, wherein the aural alarm unit includes a speech unit configured to produce a speech as the alarm.

6. The biological information measuring instrument according to claim 5, wherein:
the speech unit starts at an acquisition speech starting time a speech by which the living body recognizes a start of the acquisition of the biological information; and
the acquisition starting time comes before the acquisition speech starting time.

7. The biological information measuring instrument according to claim 1, wherein the visual alarm unit includes a motion unit configured to perform a motion calling for attention.

8. The biological information measuring instrument according to claim 1, further comprising a body movement acquisition unit configured to acquire a magnitude of a body movement of the living body, wherein if the magnitude of the body movement acquired by the body movement acquisition unit is smaller than a prescribed magnitude, the control unit allows the biological information acquisition unit to acquire the biological information.

9. The biological information measuring instrument according to claim 1, wherein the acquisition starting time comes before the alarm ending time.

10. The biological information measuring instrument according to claim 1, wherein the acquisition starting time comes before the alarm starting time.

11. The biological information measuring instrument according to claim 1, wherein the acquisition starting time comes after the alarm starting time.

12. The biological information measuring instrument according to claim 1, wherein:
the biological information acquisition unit ends the acquisition of the biological information at an acquisition ending time; and
the control unit sets the acquisition ending time so as to come before the alarm ending time.

13. The biological information measuring instrument according to claim 1, wherein the control unit controls the alarm unit to produce the alarm intermittently from the alarm starting time to the alarm ending time.

14. A method of controlling a biological information measuring instrument including: a biological information acquisition unit configured to measure a living body to acquire biological information on the living body; and an alarm unit configured to produce an alarm for reducing body movements of the living body, the method comprising the control step of controlling the biological information acquisition unit and the alarm unit,
wherein:
the alarm unit starts the alarm at an alarm starting time and ends the alarm at an alarm ending time;
the biological information acquisition unit starts acquisition of the biological information at an acquisition starting time;
the control step includes setting the acquisition starting time so as to fall in a prescribed range of time defined using the alarm starting time as a reference;
the alarm unit includes a visual alarm unit configured to perform, as the alarm, an alarm operation visually calling for attention from the living body; and
the control step includes causing the visual alarm unit to perform, as the alarm operation, an operation that calls for attention to the alarm operation without suggesting the acquisition of the biological information to the living body.

15. A control device that controls a biological information measuring instrument including: a biological information acquisition unit configured to measure a living body to acquire biological information on the living body; and an alarm unit configured to produce an alarm for reducing body movements of the living body,
the control device comprising a control unit configured to control the biological information acquisition unit and the alarm unit,
wherein:
the alarm unit starts the alarm at an alarm starting time and ends the alarm at an alarm ending time;
the biological information acquisition unit starts acquisition of the biological information at an acquisition starting time;
the control unit sets the acquisition starting time so as to fall in a prescribed range of time defined using the alarm starting time as a reference;
the alarm unit includes a visual alarm unit configured to perform, as the alarm, an alarm operation visually calling for attention from the living body; and
the control unit is configured to cause the visual alarm unit to perform, as the alarm operation, an operation that calls for attention to the alarm operation without suggesting the acquisition of the biological information to the living body.

16. A computer-readable storage medium containing a control program causing a computer to operate as the control device according to claim 15, the control program causing the computer to operate as the control unit.

* * * * *